US00PP12709P2

(12) United States Plant Patent
van den Burg

(10) Patent No.: US PP12,709 P2
(45) Date of Patent: Jun. 18, 2002

(54) LAVENDER PLANT NAMED 'BURGOLDEEN'

(75) Inventor: Gerardus Pieter van den Burg, Maasdijk (NL)

(73) Assignee: Fa van den Burg, Maasdijk (NL)

( * ) Notice: Subject to any disclaimer, the term of this patent is extended or adjusted under 35 U.S.C. 154(b) by 4 days.

(21) Appl. No.: 09/740,538

(22) Filed: Dec. 20, 2000

(51) Int. Cl.[7] ..... A01H 5/00
(52) U.S. Cl. ..... Plt./226
(58) Field of Search ..... Plt./226

(56) References Cited

PUBLICATIONS

UPOV–ROM GTITM Computer Database, 2001/04, GTI Jouve Retrieval Software, citation for 'Burgoldeen'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Lavender plant named 'Burgoldeen', characterized by its compact plant habit; unique variegated leaves with grayish green centers and creamy yellow margins; and blue purple-colored flowers.

2 Drawing Sheets

BACKGROUND OF THE INVENTION

The present Invention relates to a new and distinct cultivar of Lavender plant, botanically known as *Lavandula× intermedia Spica*, and hereinafter referred to by the name 'Burgoldeen'.

The new Lavender was discovered by the Inventor in a controlled environment in Maasdijk, The Netherlands, in July, 1998, as a naturally-occurring whole plant mutation of *Lavender×intermedia Spica* 'Grosso', not patented. The new Lavender was observed as a single plant in a group of flowering plants of the parent cultivar. The selection of this plant was based on its unique leaf variegation. Plants of the parent cultivar Gross have solid green-colored leaves.

Asexual reproduction of the new Lavender by tissue culture in a controlled environment in Maasdijk, The Netherlands, has shown that the unique features of this new Lavender are stable and reproduced true to type in successive generations.

SUMMARY OF THE INVENTION

Plants of the cultivar Burgoldeen have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Burgoldeen'. These characteristics in combination distinguish 'Burgoldeen' as a new and distinct cultivar:

1. Compact plant habit.
2. Unique variegated leaves with grayish green centers and creamy yellow margins.
3. Blue purple-colored flowers.

Compared to other Lavender cultivars known to the Inventor, plants of the new Lavender are more compact; in addition, plants of the new Lavender have smaller and variegated leaves.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Lavender.

The photograph on the first sheet comprises a side perspective view of a typical flowering plant of 'Burgoldeen' grown in a container.

The photograph at the top of the second sheet comprises a close-up view of typical flowering spikes of 'Burgoldeen'.

The photograph at the bottom of the second sheet comprises a close-up view of typical leaves of 'Burgoldeen'.

DETAILED BOTANICAL DESCRIPTION

In the following description, color references are made to The Royal Horticultural Society Colour Chart, 1995 Edition, except where general terms of ordinary dictionary significance are used. Plants were grown in a glass-covered greenhouse and under conditions which closely approximate commercial production conditions in Maasdijk, The Netherlands. Day temperatures averaged 20° C., night temperatures averaged 10° C., and light levels were about 450 kilo joules. Plants used for this description were grown for about 9 months old and grown in a 5-liter container.

Botanical classification: *Lavandula×intermedia Spica* cultivar Burgoldeen.

Parentage: Naturally-occurring whole plant mutation of *Lavandula×intermedia Spica* cultivar Grosso, not patented.

Propagation:

*Type cutting.*—By tissue culture.

*Time to initiate roots on tissue-cultured micro cuttings.*—Summer: About 21 days at 34° C. Winter: About 35 days at 17° C.

*Time to produce a rooted liner from tissue-cultured micro cuttings.*—Summer: About 35 days at 20° C. Winter: About 56 days at 15° C.

*Root description.*—Freely branching.

Plant description:

*Form.*—Perennial plant; compact, upright and spreading plant habit. Flowers arranged on erect verticillate spikes. Freely branching with lateral branches potentially forming at every node; dense and bushy growth habit.

*Crop time.*—From planting, about 9 months are required to produce finished flowering plants in 5-liter containers.

*Plant height* (*soil level to top of plant plane*).—About 80 cm.

*Plant diameter.*—About 50 cm.

*Vigor.*—Moderately vigorous.

*Lateral branches.*—Length: About 20 cm. Diameter: About 2 mm. Internode length: About 1.7 cm. Texture: Glabrous. Color: 138A to 191A.

*Foliage description.*—Simple, opposite, decurrent. Quantity per lateral stem: About 14. Length: About 5 cm. Width: About 5 mm. Shape: Linear to oblanceolate. Apex: Acute. Base: Cuneate. Margin: Entire. Texture: Both surfaces, puberulous. Fragrance: Aromatic, typical of genus. Color: Upper and lower surfaces: Grayish green centers, 191B, surrounded at creamy yellow margins, 11B or 160B. Creamy yellow variegation covers about 30 to 40% of the leaf.

Flower description:

*Flower arrangement and shape.*—Small single labiate flowers arranged on verticillate spikes; about 64 flowers per spike; mature plants typically produce 25 to 100 flowering stems per plant.

*Natural flowering season.*—Late summer, flowering continuous.

*Flower longevity on the plant.*—Longevity of individual flowers is highly dependent on weather conditions, typically about 4 weeks. Flowers persistent.

*Spike length.*—About 80 cm.

*Flower buds.*—Length: About 5 mm. Diameter: About 2 mm. Shape: Oblong to oval. Color: 191B.

*Flowers.*—Length: About 1 cm. Diameter: About 6 mm. Fragrance: Aromatic, typical of genus.

*Petals.*—Arrangement: Five in a single whorl; fused. Length: About 6 mm. Width: About 1.8 mm. Shape: Oval to deltoid; labiate. Apex: Rounded to obtuse. Margin: Entire. Texture: Pubescence on lower surface; slightly ribbed. Color: When opening and fully opened upper surface: 88A to 90B. When opening and fully opened lower surface: 90C to 90D.

*Sepals.*—Arrangement: Five in a single whorl; fused. Calyx length: About 1 cm. Calyx diameter: About 6 mm. Shape: Oblong, labiate. Apex: Rounded. Margin: Entire. Texture: Ribbed; glandular. Color: Upper surface: 191B. Lower surface: 137C to 138A.

*Pedicels.*—Strength: Strong. Angle: About 10 to 20° from main stem. Length: About 1 mm. Diameter: Less than 1 mm. Color: 138A.

*Reproductive organs.*—Stamens: Quantity: Four. Anther shape: Oval to reniform; dorsifixed. Anther length: Less than 0.5 mm. Anther color: Orange brown. Pollen: Scarce. Pollen color: Orange brown. Pistils: Quantity: One. Pistil length: About 6 mm. Stigma shape: Oblong. Stigma color: Greyish white. Style length: About 5 mm. Style color: Greyish white. Ovary color: Light green. Seed: Seed development has not been observed.

Disease resistance: Plants of the new Lavender have not been noted to be resistant to pathogens common to Lavender.

It is claimed:

1. A new and distinct cultivar of Lavender plant named 'Burgoldeen', as illustrated and described.

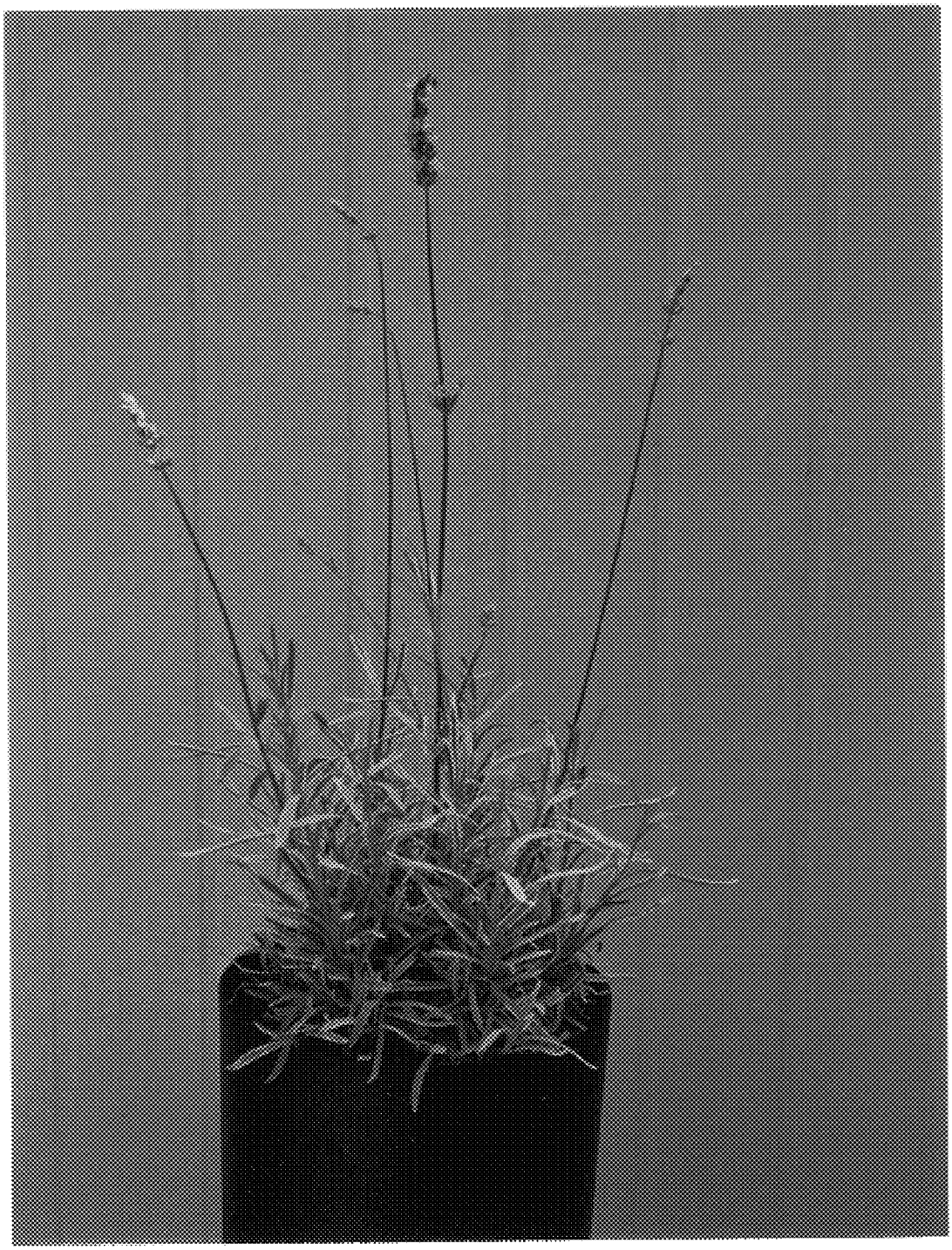

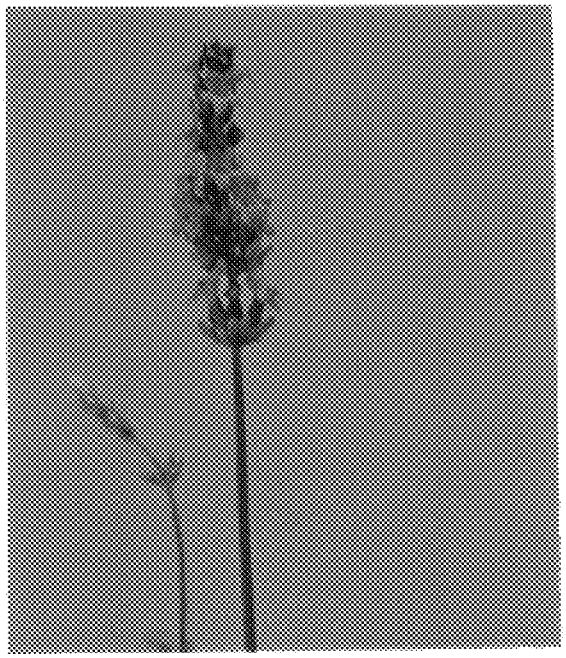
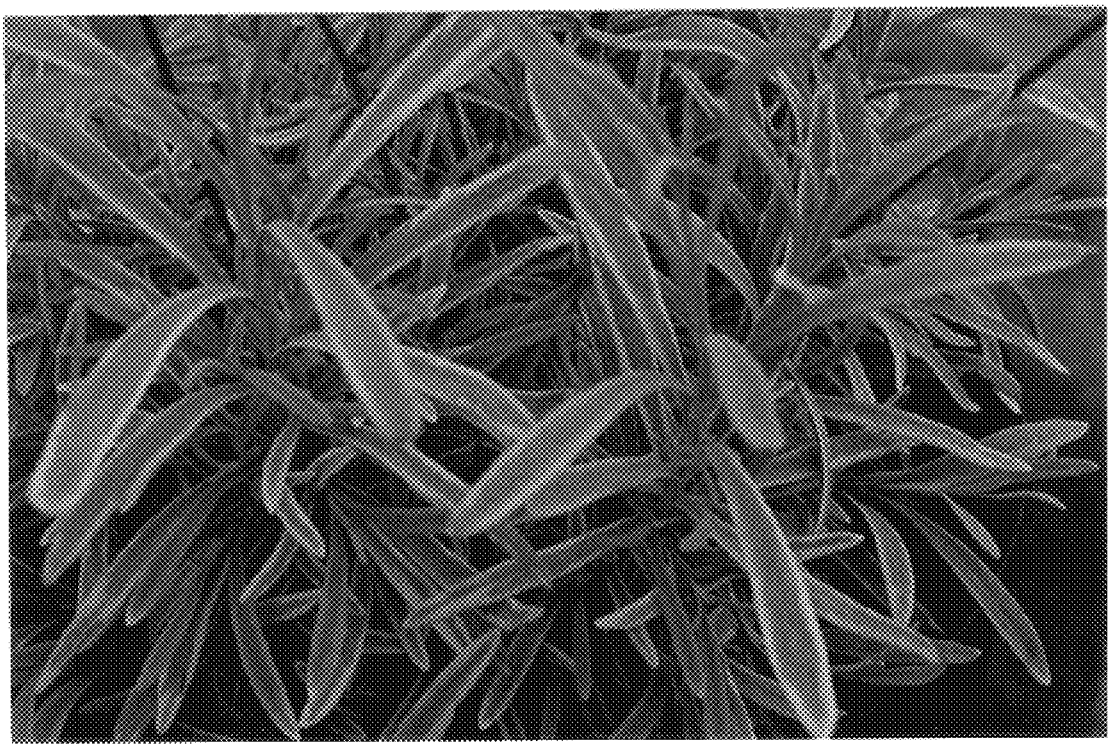

* * * * *